United States Patent [19]

Lachhein et al.

[11] Patent Number: 4,824,949
[45] Date of Patent: Apr. 25, 1989

[54] PROCESS FOR THE PREPARATION OF PYRIMIDINES

[75] Inventors: Stephen Lachhein, Hofheim am Taunus; Lothar Willms, Hillscheid, both of Fed. Rep. of Germany

[73] Assignee: Hoechst Aktiengesellschaft, Frankfurt, Fed. Rep. of Germany

[21] Appl. No.: 132,483

[22] Filed: Dec. 14, 1987

[30] Foreign Application Priority Data

Dec. 16, 1986 [DE] Fed. Rep. of Germany ....... 3642830

[51] Int. Cl.$^4$ .......................................... C07D 239/47
[52] U.S. Cl. ..................................... 544/320; 544/321
[58] Field of Search ................. 544/320, 321; 548/337

[56] References Cited

U.S. PATENT DOCUMENTS

| 3,985,785 | 10/1976 | Edenhofer et al. | 544/326 |
|---|---|---|---|
| 4,032,559 | 6/1977 | McCall et al. | 544/402 |
| 4,169,179 | 9/1979 | Bussey, Jr. | 428/159 |
| 4,492,598 | 1/1985 | Willms et al. | 544/211 |

FOREIGN PATENT DOCUMENTS

| 0024200 | 2/1981 | European Pat. Off. |
| 0071958 | 2/1983 | European Pat. Off. |
| 2426913 | 12/1975 | Fed. Rep. of Germany |

OTHER PUBLICATIONS

Braker et al., J.A.C.S. vol. 69, pp. 3072–3078 (1947) "Substituted Sulfanilamidopyrimidines".
Fisher et al., J.A.C.S. vol. 54 pp. 727–733 (1932) "Researches on pyrimidines . . . ".
Sharanin et al., Chem. Abst. 108-204588f (1988).
Chem. Pharm. Bull., "Studies on Antitumor Substances. Reaction of N-Amidino-O-alkylisourea with Some Carboxylic Esters", Hayashi et al., vol. 16 (3), p. 474 (1968).
J. Am. Chem. Soc., "Orthoesters and Related Compounds from Malono- and Succinonitriles", S. M. McElvain and Juel P. Schroeder, vol. 71, p. 40 (1949).

Primary Examiner—Donald G. Daus
Assistant Examiner—Cecilia Shen
Attorney, Agent, or Firm—Curtis, Morris & Safford

[57] ABSTRACT

Process for the preparation of pyrimidines
Pyrimidines of the formula 1

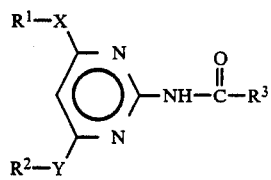

in which X and Y, independently of one another, denote oxygen or sulfur, $R^1$ and $R^2$, independently of one another, denote ($C_1$—$C_4$) alkyl, ($C_1$—$C_4$-alkoxy)-$C_1$—$C_2$-alkyl or halo-$C_1$—$C_4$-alkyl, and $R^3$ denotes $C_1$—$C_4$-alkyl, phenyl or phenoxy which may both be substituted by one, two or three radicals from the series comprising halogen, $C_1$—$C_4$-alkoxy and $C_1$—$C_4$-alkyl radicals, halo-$C_1$—$C_4$-alkyl or $C_1$—$C_4$-alkoxy, are obtained in a process in which propanediimidates of the formula II

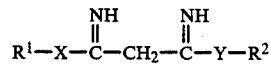

or salt thereof, are reacted with N-cyanoamides of the formula NC—NR$^4$—CO—R$^3$ in which R$^4$ denotes hydrogen or a cation, in an inert solvent. The compounds of the formula I are suitable as intermediates for the preparation of herbicidal sulfonylureas.

16 Claims, No Drawings

PROCESS FOR THE PREPARATION OF PYRIMIDINES

DESCRIPTION

The invention relates to a process for the preparation of pyrimidines of the formula I

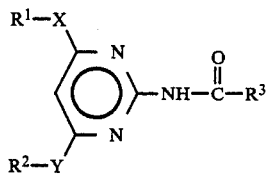

in which

X and Y, independently of one another, denote oxygen or sulfur, $R^1$ and $R^2$, independently of one another, denote $(C_1-C_4)$alkyl, $(C_1-C_4)$alkoxy-$(C_1-C_2)$alkyl or halo$(C_1-C_4)$alkyl, and $R^3$ denotes $(C_1-C_4)$alkyl, phenyl or phenoxy which may both be substituted by one, two or three radicals from the series comprising halogen, $(C_1-C_4)$alkoxy and $(C_1-C_4)$alkyl radicals, halo$(C_1-C_4)$alkyl or $(C_1-C_4)$alkoxy, wherein a propanediimidate of the formula II

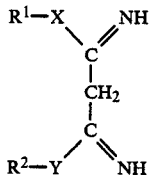

in which $R^1$ and $R^2$ are as defined in the formula I, or one of its salts, is reacted with an N-cyanoamide of the formula III

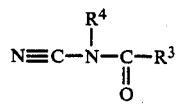

in which $R^4$ denotes H or a cation, in an inert solvent.

Compounds of the formula I are valuable intermediates in the preparation of sulfonylureas having a herbicidal action (U.S. Pat. No. 4,169,719, and EP-A No. 071,958 (U.S. Pat. No. 4,492,598)).

The preparation of the compounds I via the corresponding aminopyrimidines is known, the latter being prepared by reaction of propanediimidates with aqueous cyanamide solution or cyanogen chloride in a two-step or three-step process (EP-A-No. 0,024,200). The formation and subsequent isolation of an N-cyanoimidate as an intermediate are characteristic process features of this process. However, the amino pyrimidine yields obtained in this process are unsatisfactory, inter alia as a consequence of a not inconsiderable amount of by-products.

Surprisingly, the process according to the invention proceeds, in contrast, as a technically simple one-step process without intermediates which can be isolated, and gives the acylated compounds I directly. By-products are formed only to a minor extent. After completion of the reaction and subsequent filtration, the final product remains in high purity.

In the process according to the invention, no N-cyanoimidate is formed as an intermediate, in contrast to the known process described above. The high selectivity during formation of compounds of the formula I, and the high yields associated with this, were unexpected. Rather, the formation of by-products was expected, since it was known that, in related reactions—the reaction of guanyl-O-alkylisoureas in place of imidates with cyanocarboxylates—the imide nitrogen reacts exclusively with the carboxyl group with triazine formation (Chem. Pharm. Bull. 16 (3), 474 (1969)).

The process according to the invention is expediently carried out by isolating the propanediimidate as the mono salt or disalt or as the bisimidate, and reacting it in solution or as a suspension with the N-cyanoamides of the formula III at reaction temperatures of 0°–100° C., preferably 10°–80° C., and pHs of 1–8, preferably 2–7. Preferred salts of the propane diimidate are those of hydrofluoric acid, hydrochloric acid or hydrobromic acid, of sulfuric acid or phosphoric acid. Haloalkyl radicals $R^1$, $R^2$ and $R^3$ are, for example, $CH_2Cl$, $CHCl_2$, $CCl_3$, $CH_2-CH_2Cl$ or $CH_2CF_3$. X and Y preferably denote oxygen. $R^1$, $R^2$ and $R^3$ preferably in each case denote $(C_1-C_4)$alkyl, in particular methyl. Cations for the $R^4$ radical are, for example, alkali metal cations and alkaline-earth metal cations, in particular $Na^+$, $K^+$ and $\frac{1}{2}Mg^{2+}$.

Suitable inert solvents are those which are inert under the particular reaction conditions. For example, the solvents used can be water, alcohols, such as methanol and ethanol, ketones, such as acetone and methyl isobutyl ketone, halogenated hydrocarbons, such as methylene chloride and chloroform, ethers, such as diethyl ether, dioxane and tetrahydrofuran, esters, such as methyl acetate, ethyl acetate and butyl acetate, hydrocarbons, such as toluene, xylene, hexane and cyclohexane, nitriles, such as acetonitrile, acids, such as formic acid and glacial acetic acid, or mixtures of at least two of the solvents mentioned.

In order to prevent the interfering influence of oxygen on the reaction, it is expedient to work under an inert gas atmosphere, for example under nitrogen.

The compounds of the formula II can be prepared by known methods (S. M. McElvain and I. D. Schroeder, JACS 71, 40 (1949); B. Harstun, DE-A-No. 2,426,913). The monosalt and the bisimidate of these compounds can be prepared from the corresponding disalt through reaction with bases such as alkali metal hydroxides, carbonates, hydrogen carbonates or alcoholates and alkalne-earth metal hydroxides, carbonates, hydrogen carbonates or alcoholates, in a solvent which is inert under the reaction conditions.

The compounds of the formula III can be prepared by known methods through reaction of cyanamide with the appropriate acyl chloride.

The following examples are intended to illustrate the process according to the invention in greater detail:

Example 1

179.4 g of methyl chloroformate and 586 g of 25% strength sodium hydroxide solution are added simultaneously to 154.8 g of an aqueous 50% strength cyanamide solution in 300 ml of water at 40° C. and a pH of 6.5–7.5 under a blanket of nitrogen. 315.0 g of dimethylpropanediimidate monohydrochloride are then added, and the mixture is kept at 60° C. and a pH of 5.0 for 2 hours. After cooling to room temperature, the pH is adjusted to 7 using 2N sodium hydroxide solution, and the solid product is filtered off. The yield of the dried product is 366 g (≙91% yield). The melting point is 93°-94° C.

Example 2

222.4 g of dimethylpropanediimidate dihydrochloride are added slowly to a suspension of 70.4 g of sodium hydrogen carbonate in 920 ml of water at 0° C. 520 ml of a cyanamide carboxylate solution, prepared from 96 g of a 50% strength aqueous cyanamide solution and 121.2 g of methyl chloroformate, are added to this mixture at room temperature. After heating at 80° C. for 3 hours at a pH of 4, the mixture is neutralized using the 2N sodium hydroxide solution, and the solid product is filtered off. 209 g of product are obtained (≙90% yield). The melting point is 93°-94° C.

Example 3

231 g of 50% strength sodium carbonate solution are slowly added dropwise to a suspension of 222.4 g of dimethylpropanediimidate dihydrochloride in 1,000 ml of chloroform at 0° C. 520 ml of a cyanamide carboxylate solution, prepared from 96 g of a 50% strength aqueous cyanamide solution and 121.9 g of methyl chloroformate, are added to this 2-phase mixture. The mixture is heated at 60° C. for 4 hours, the phases are separated, and the organic phase is freed from solvent.

172 g of product of melting point 93°-94° C. remain (≙90% yield).

Example 4

179.4 g of methyl chloroformate and 586 g of 25% strength sodium hydroxide solution are added simultaneously to 154.8 g of an aqueous 50% strength cyanamide solution in 300 ml of water at 40° C. and a pH of 6.5-7.5 under a blanket of nitrogen. 383 g of dimethylpropanediimidate dihydrochloride are then added at 0° C., and the mixture is kept at 70° C. for 3 hours at a pH of 5.0. After cooling to room temperature, the pH of the mixture is adjusted to 7 using sodium hydroxide solution, and the solid product is filtered off. The yield of the dried product is 367 g (≙91% yield). The melting point is 93°-94° C.

The following compounds of the formula I can be prepared analogously to the procedures described in Examples 1-4:

| EXAMPLE | X | Y | $R^1$ | $R^2$ | $R^3$ |
|---|---|---|---|---|---|
| 5 | O | O | $CH_3$ | $CH_3$ | $OCH_3$ |
| 6 | O | O | $C_2H_5$ | $C_2H_5$ | $OCH_3$ |
| 7 | O | O | $C_2H_5$ | $C_2H_5$ | $CH_3$ |
| 8 | O | O | $CH_3$ | $CH_3$ | $O-C_6H_5$ |
| 9 | O | O | $C_2H_5$ | $C_2H_5$ | $O-C_6H_5$ |
| 10 | O | O | $CH_3$ | $CH_3$ | $CH_2Cl$ |
| 11 | O | O | $CH_3$ | $CH_3$ | $CHCl_2$ |
| 12 | O | O | $CH_3$ | $CH_3$ | $CCl_3$ |
| 13 | O | O | $CH_3$ | $CH_3$ | $OC_2H_5$ |
| 14 | S | S | $C_2H_5$ | $C_2H_5$ | $OCH_3$ |
| 15 | O | O | $CH-CH_3$<br>$\|$<br>$CH_3$ | $CH-CH_3$<br>$\|$<br>$CH_3$ | $OCH_3$ |
| 16 | O | S | $CH_3$ | $CH_3$ | $OCH_3$ |
| 17 | O | S | $C_2H_5$ | $C_2H_5$ | $OCH_3$ |
| 18 | O | O | $CH_3$ | $CH_3$ | $OC_2H_5$ |
| 19 | O | O | $C_2H_5$ | $C_2H_5$ | $OC_2H_5$ |
| 20 | O | O | $CH_2Cl$ | $CH_2Cl$ | $OCH_3$ |
| 21 | O | O | $CH_2Cl$ | $CH_2Cl$ | $OC_2H_5$ |
| 22 | O | O | $CH_2Cl$ | $CH_2Cl$ | $O-C_6H_5$ |
| 23 | S | S | $CH_2Cl$ | $CH_2Cl$ | $OCH_2Cl$ |
| 24 | O | O | $CF_3$ | $CF_3$ | $OCH_3$ |
| 25 | O | O | $CF_3$ | $CF_3$ | $OC_2H_5$ |
| 26 | S | S | $CF_3$ | $CF_3$ | $OC_2H_5$ |
| 27 | O | O | $CH_2OCH_3$ | $CH_2OCH_3$ | $OCH_3$ |
| 28 | O | S | $CH_2OC_2H_5$ | $CH_2OC_2H_5$ | $OCH_3$ |
| 29 | O | O | $CH_2OC_2H_5$ | $CH_2OCH_3$ | $OC_2H_5$ |

We claim:

1. A process for the preparation of a compound of the formula I

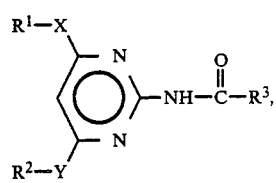

in which

X and Y, independently of one another, are oxygen or sulfur, $R^1$ and $R^2$, independently of one another, are $(C_1-C_4)$-alkyl, $(C_1-C_4)$alkoxy-$(C_1-C_2)$alkyl or halo$(C_1-C_4)$alkyl, and $R^3$ is $(C_1-C_4)$alkyl, phenyl or phenoxy which may both be substituted by one, two or three radicals from the series comprising halogen, $(C_1-C_4)$alkoxy or $(C_1-C_4)$alkyl radicals, halo$(C_1-C_4)$alkyl or $(C_1-C_4)$alkoxy, wherein a propanediimidate of the formula II

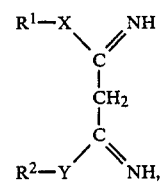

in which $R^1$ and $R^2$ are as defined in the formula I, or one of its salts, is reacted with an N-cyanoamide of the formula III

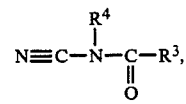

in which $R^4$ is H or a cation, in an inert solvent.

2. The process as claimed in claim 1, wherein, in formula I, X and Y in each case are oxygen and $R^1$, $R^2$ and $R^3$ in each case are $(C_1-C_4)$alkyl.

3. The process as claimed in claim 1, wherein $R^4$ is H in formula III.

4. The process as claimed in claim 1, wherein the inert solvent used is water, an alcohol, a ketone, a hydrocarbon, a halogenated hydrocarbon, an ether, an ester, a nitrile, a carboxylic acid or a mixture of at least two of the solvents mentioned.

5. The process as claimed in claim 1, wherein the solvent used is water, chloroform, methanol, acetone, tetrahydrofuran, acetonitrile or a mixture of at least two of the solvents.

6. The process as claimed in claim 1, wherein the reaction temperature is 0°-100° C.

7. The process as claimed in claim 1, wherein the reaction temperature is 10°-80° C.

8. The process as claimed in claim 1, wherein the pH is 1-8.

9. The process as claimed in claim 1, wherein the pH is 2-7.

10. The process as claimed in claim 1, wherein the reaction is carried out under an inert gas atmosphere.

11. A process as claimed in claim 1, wherein X and Y are oxygen and $R^1$, $R^2$ and $R^3$ are $(C_1-C_4)$alkyl and the inert solvent used is water, an alcohol, a ketone, a hydrocarbon, a halogenated hydrocarbon, an ether, an ester, a nitrile, a carboxylic acid or a mixture of at least two of the solvents mentioned.

12. A process as claimed in claim 11, wherein the reaction temperature is 0°-100° C.

13. A process as claimed in claim 11, wherein the reaction is carried out under an inert gas atmosphere.

14. A process as claimed in claim 11, wherein the pH is 1-8.

15. A process as claimed in claim 11, wherein the reaction temperature is 10°-80° C., the pH 2-7 and the reaction is carried out under inert gas atmosphere.

16. A process as claimed in claim 15, wherein the solvent used is water, chloroform, methanol, acetone, tetrahydrofuran, acetonitrile or a mixture of at least two of the solvents mentioned.

* * * * *